US 8,555,880 B2

(12) United States Patent
Boring

(10) Patent No.: US 8,555,880 B2
(45) Date of Patent: Oct. 15, 2013

(54) VARIABLE TRANSITION PRESSURE PROFILES FOR A BI-LEVEL BREATHING THERAPY MACHINE

(75) Inventor: Joseph J. Boring, Davidsville, PA (US)

(73) Assignee: DeVilbiss Healthcare, LLC, Somerset, PA (US)

( * ) Notice: Subject to any disclaimer, the term of this patent is extended or adjusted under 35 U.S.C. 154(b) by 513 days.

(21) Appl. No.: 12/845,200

(22) Filed: Jul. 28, 2010

(65) Prior Publication Data

US 2012/0024286 A1    Feb. 2, 2012

(51) Int. Cl.
*A61M 16/00* (2006.01)
(52) U.S. Cl.
USPC .................................................. 128/204.21
(58) Field of Classification Search
USPC ............. 128/204.18, 204.21, 204.22, 204.23, 128/204.26, 203.14
See application file for complete search history.

(56) References Cited

U.S. PATENT DOCUMENTS

| 5,865,173 | A | 2/1999 | Froehlich |
| 7,296,573 | B2 | 11/2007 | Estes et al. |
| 8,122,885 | B2 * | 2/2012 | Berthon-Jones et al. 128/204.26 |
| 2003/0127097 | A1 * | 7/2003 | Yurko ....................... 128/204.23 |
| 2005/0211249 | A1 * | 9/2005 | Wagner et al. ........... 128/204.23 |

FOREIGN PATENT DOCUMENTS

| WO | 0174430 A1 | 10/2001 |
| WO | 2010021556 A1 | 2/2010 |
| WO | 2010-067236 A1 | 6/2010 |

* cited by examiner

*Primary Examiner* — Jackie Ho
*Assistant Examiner* — Mark Wardas
(74) *Attorney, Agent, or Firm* — Fox Rothschild LLP; Dennis M. Carleton

(57) ABSTRACT

A method for controlling the transitions between two different pressures supplied by a breathing therapy device using a transition pressure profile for which the basic shape, the magnitude and the duration may be controlled by a user of the device or the user's therapist.

13 Claims, 9 Drawing Sheets

VARIABLE TRANSITION PRESSURE PROFILES FOR A BI-LEVEL BREATHING THERAPY MACHINE

FIELD OF THE INVENTION

This invention is related to the field of breathing gas delivery machines, such as continuous positive airway pressure (CPAP) or bi-level positive airway pressure (Bi-PAP) machines of the type typically used to treat patients suffering from breathing disorders, such as hypopnea or apnea, and, in particular, is related to controlling the shape of the curve representing the pressure delivered to the patient.

BACKGROUND OF THE INVENTION

Continuous Positive Airways Pressure (CPAP) machines are well known in the art for use in the treatment of a number of respiratory conditions, such as sleep apnea and hypopnea, by supplying a continuous positive pressure to a patient's airway while the patient sleeps. A typical CPAP apparatus is programmed with a CPAP therapy pressure, and is able to maintain the set pressure (measured either at the mask or at a base unit) during the inhalation and exhalation phases of the breathing cycle.

In a variation of the basic CPAP machine, two air pressure levels are able to be programmed into the machine, an inspiratory positive airway pressure (IPAP), delivered during the inhalation phase of the breathing cycle, and a expiratory positive airway pressure (EPAP), delivered during the exhalation phase of the breathing cycle. Typically, the EPAP pressure is lower than the IPAP pressure, resulting in a pressure profile over time having a square wave shape, as shown in FIG. 2.

This arrangement tends to increase the patient's comfort while using the machine by providing the lowest possible EPAP pressure necessary to maintain airway patency, thereby reducing the work required for the patient to exhale. Typically, the machine is able to sense the patient's breathing rhythm, and is able to detect the transitions between the inhalation and exhalation phases of the breathing cycle, such that the proper pressure can be delivered to the patient. This version of the CPAP machine is often referred to as a Bi-Level PAP or Bi-PAP machine.

One problem with the typical Bi-Level PAP machine is that the transitions between the IPAP and EPAP pressures can be abrupt, causing discomfort to the patient, especially when transitioning from the EPAP to the IPAP pressure. Attempts have been made to solve this problem by providing a means for adjusting the transitions between the EPAP and IPAP pressures. As an example, U.S. Pat. No. 5,865,173 provides a means for the therapist to select a rounding factor that is applied to the pressure waveform to smooth the transitions between the two pressures. Various degrees of rounding may be selected to maximize the patient's comfort. Likewise, U.S. Pat. No. 7,296,573 provides a set of pre-defined pressure contours which are stored in the unit's memory and which may be selected by the therapist to maximize both the patient's comfort and also the effectiveness of the therapy. Both the '173 patent and the '573 patent have limitations in their ability to customize the shape of the pressure curve. Therefore, it would be desirable to provide a method of selecting the waveform that provides increased flexibility to further maximize both the patient's comfort and the effectiveness of the therapy delivered to the patient.

SUMMARY OF THE INVENTION

The present invention represents an improvement on the rounding scheme disclosed in the '173 patent. The main difference is that the contours for the transitions between the inhalation and exhalation phases of the breathing cycle, instead of being rounded, are generated by the calculation of a third order polynomial having coefficients selected to achieve several different shaped profiles, allowing the therapist to select the profile that maximizes the comfort for the patient while still achieving the goals of the therapy. The points on the contour are calculated as a percentage between the IPAP and EPAP pressures, with the inhale profiles starting at the EPAP pressure and ending at the IPAP pressure, and the exhale profiles starting at the IPAP pressure and ending at the EPAP pressure.

In addition, the profiles for the transitions may be applied in advance of the detection of each subsequent phase of the breathing cycle. In other words, the beginning of the next phase of the breathing cycle is anticipated based on the measured length of the phases of previous cycles, and the profile is applied starting prior to the anticipated end of the current phase. The percentage of the current phase marking the start of the application of the profile is a settable parameter.

In a like manner, the profile may extend past the detected start of the next phase. The percentage of the next phase marking the end of the profile is also a settable parameter in the system.

Some or all of the settable parameters defining the pressure profile and defining the starting and ending points of profiles may be set by either the patient or the therapist. The system is capable of estimating the length of the overall breathing cycle, as well as the inhalation phase and the exhalation phase of the breathing cycle, all based on a measurement of one or more previous breathing cycles.

DETAILED DESCRIPTION OF THE INVENTION

Figure 1:
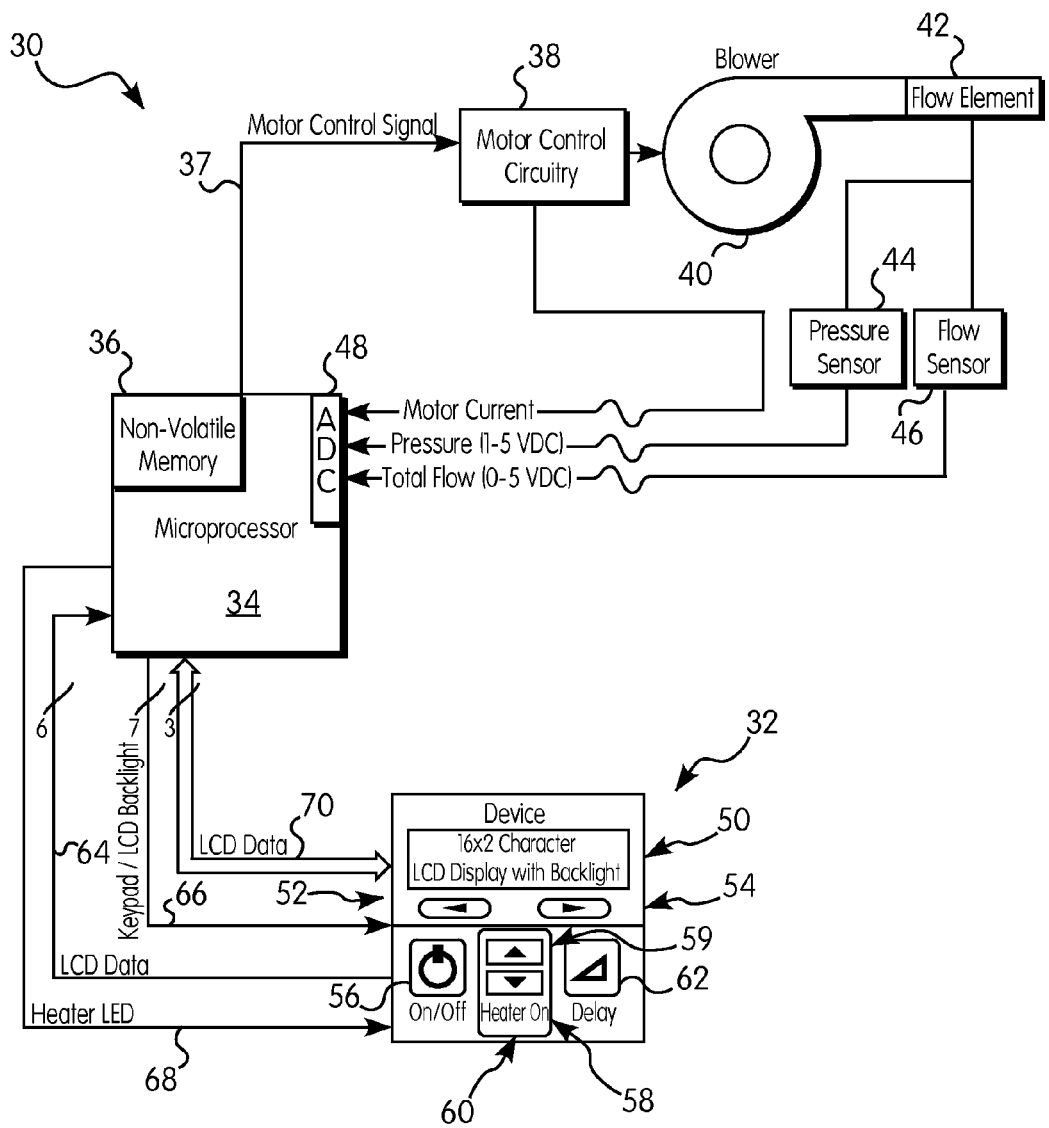
FIG. 1 is a schematic depiction of a typical prior art CPAP machine of the type that would be employed with the present invention

FIG. 1 is a block diagram of a typical breathing therapy device on which the present invention could be implemented. The device includes a main unit 30 housing microprocessor 34 and related non-volatile memory 36, as well as blower 40 and motor control circuitry 38. The device 30 is typically equipped with a user interface panel 32 which may be used to control the device as well as to program various operating parameters into the device.

Microprocessor 34 runs software stored in non-volatile memory 36, which implements the algorithms controlling blower 40 to regulate the pressure being delivered to the user of the device. The present invention could be implemented as a control algorithm stored as software in non-volatile memory 36 and executed by microprocessor 34.

Figure 1A:
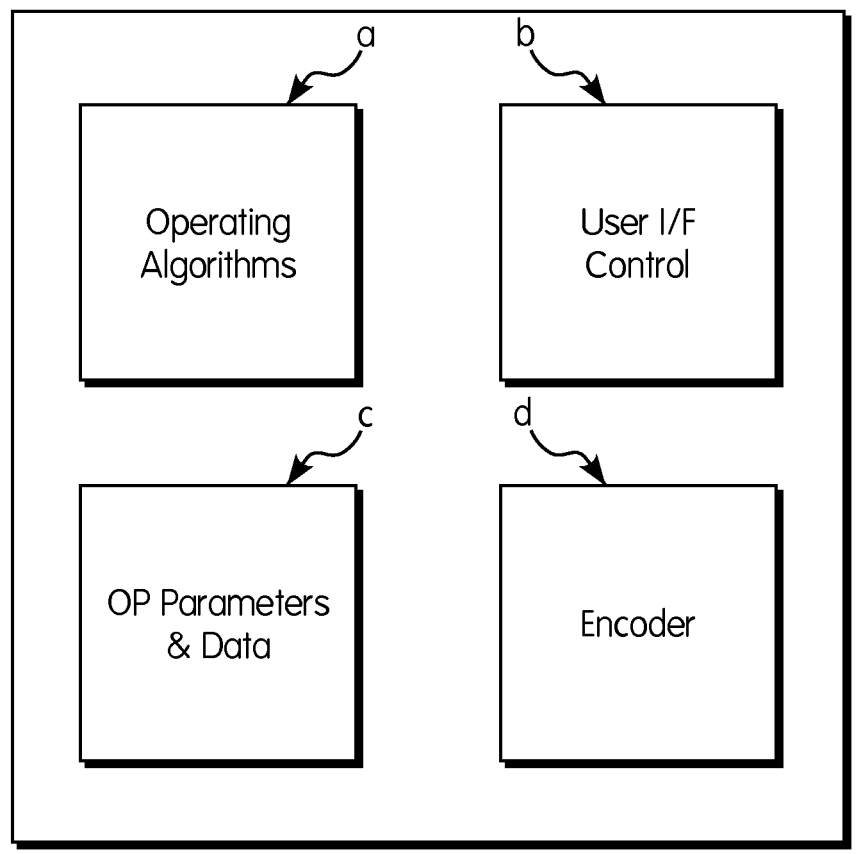
FIG. 1a is a block diagram showing one potential organization of the non-volatile memory of the device of FIG. 1.

Microprocessor 34 and non-volatile memory 36 control the functioning of the unit. Non-volatile memory 36 may be broken down as shown in FIG. 1a and includes operating algorithms 36a, user interface control 36b, encoder 36c and storage for operating parameters and collected data 36d. As will be realized by one of skill in the art, many configurations for the structure of non-volatile memory are possible. In one possible alternative embodiment, the unit may be provided with a separate microprocessor or Application Specific Integrated Circuit (ASIC) dedicated to the collection, storage and manipulation of the system parameters and selected operating data (not shown). Such dedicated components may use either the original memory hardware 36 or a separate dedicated memory for storing the data. Memory for the storage of operating algorithms and collected data can include any type of memory well known in the art, including non-volatile RAM, flash media and hard drives, any of which may be internal or external to the device.

Operating algorithms 36a control the varying of the pressure in flow element 42 based on a monitoring of the user's breathing patterns, as sensed by pressure sensor 44 and flow sensor 46. The actual algorithms will vary from unit to unit. The present invention may be implemented as an algorithm stored in the operating algorithms 36a section of non-volatile memory 36.

Microprocessor 34 is electrically connected to motor control circuitry 38 that, in turn, is electrically connected to blower 40. Blower 40 provides pressurized breathing gas to the flexible tube (not shown) via flow element 42. Motor control circuitry 38 is operative to control the speed of blower 40, and, thus, the pressure and flow rate of the air forced into flow element 42. Alternatively, pressure and flow rate may be controlled by a check valve disposed within flow element 42.

Pressure sensor 44 and flow sensor 46 are provided to monitor the pressure and flow rate, respectively, of the air passing through flow element 42 and to provide that information to microprocessor 34. Feedback voltages representing the blower motor current, the air pressure and the air flow rate are supplied by motor control circuitry 38, pressure sensor 44 and flow sensor 46, respectively, to an analog to digital converter 48 that converts the data to a digital format for use by operating algorithms 36a and for storage in data storage memory 36d.

Figure 2:
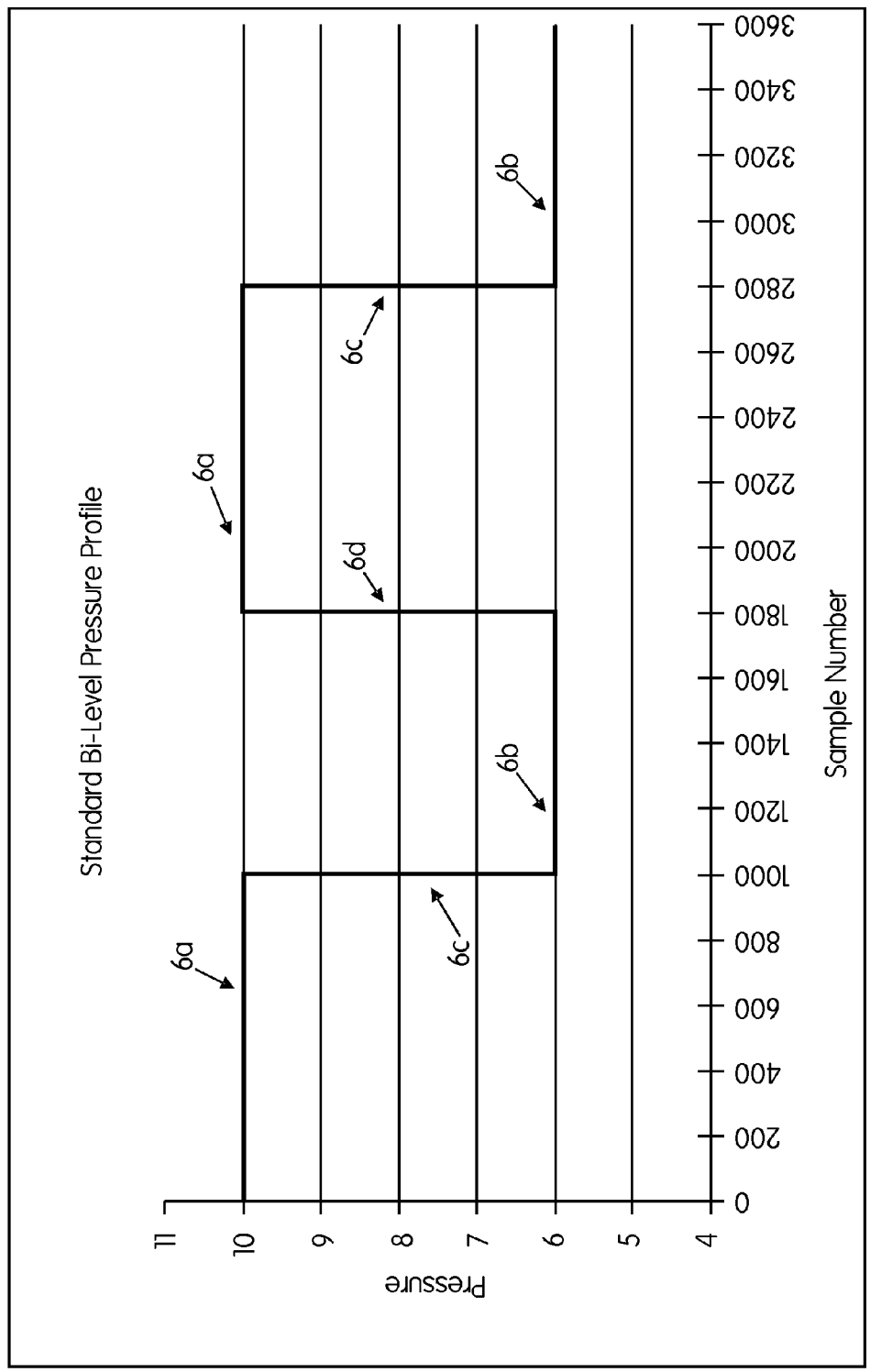
FIG. 2 illustrated a standard bi-level pressure profile.

On a typical bi-level PAP machine the user or therapist is able to set both the pressure delivered during the inhalation phase of the breathing cycle (IPAP) and the pressure delivered during the exhalation phase of the breathing cycle (EPAP). The use of just the IPAP and EPAP pressures will result in a square wave pressure profile as shown in FIG. 2. FIG. 2 shows two complete breathing cycles showing IPAP pressure 6a at 10 cm-$H_2O$ and the EPAP pressure 6b at 6 cm-$H_2O$. The transition between the IPAP pressure 6a and EPAP pressure 6b is shown as 6c and the transition between exhale pressure 6b and inhale pressure 6a is shown as 6d in FIG. 2. The objective of the present invention is to replace transitions 6c and 6d with customizable profiles, referred to herein as a transition pressure profiles, to make the transition between the inhale phase and exhale phase and between the exhale phase and inhale phase easier and more comfortable for the user of the device.

Figure 3:
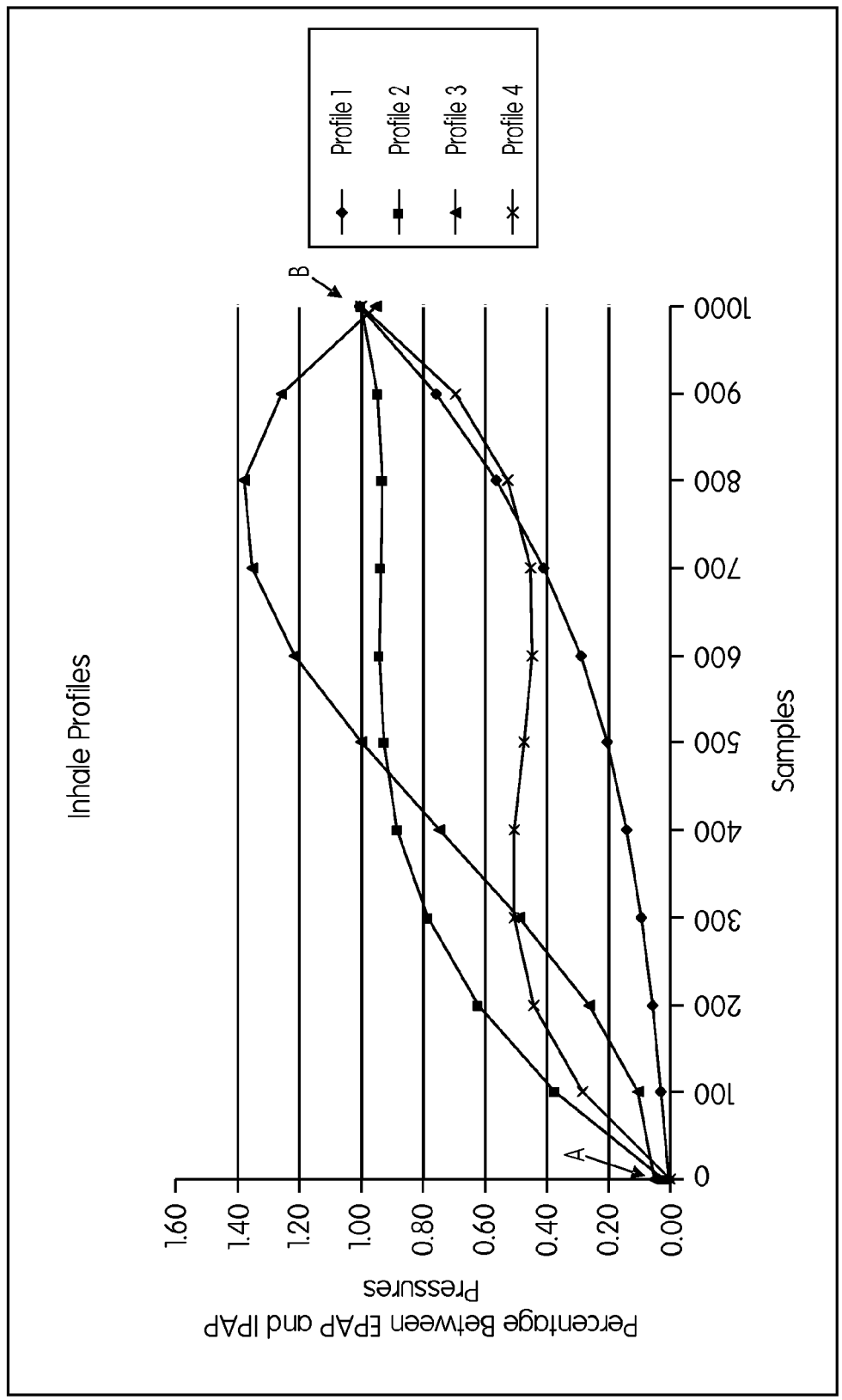
FIG. 3 illustrates several possible inhalation profiles I accordance with the present invention.
Figure 4:
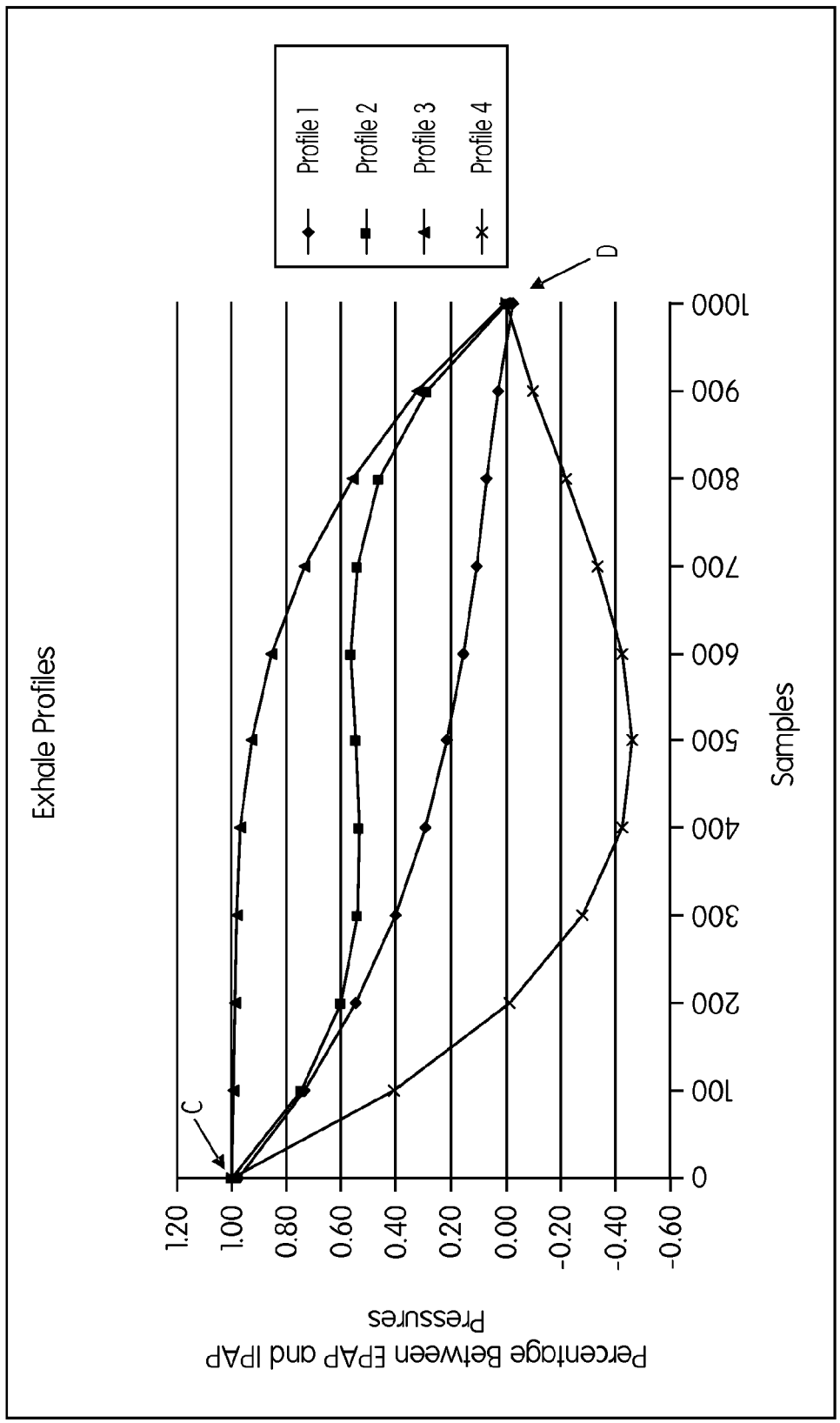
FIG. 4 illustrates several possible exhalation profiles in accordance with the present invention.
Figure 5:
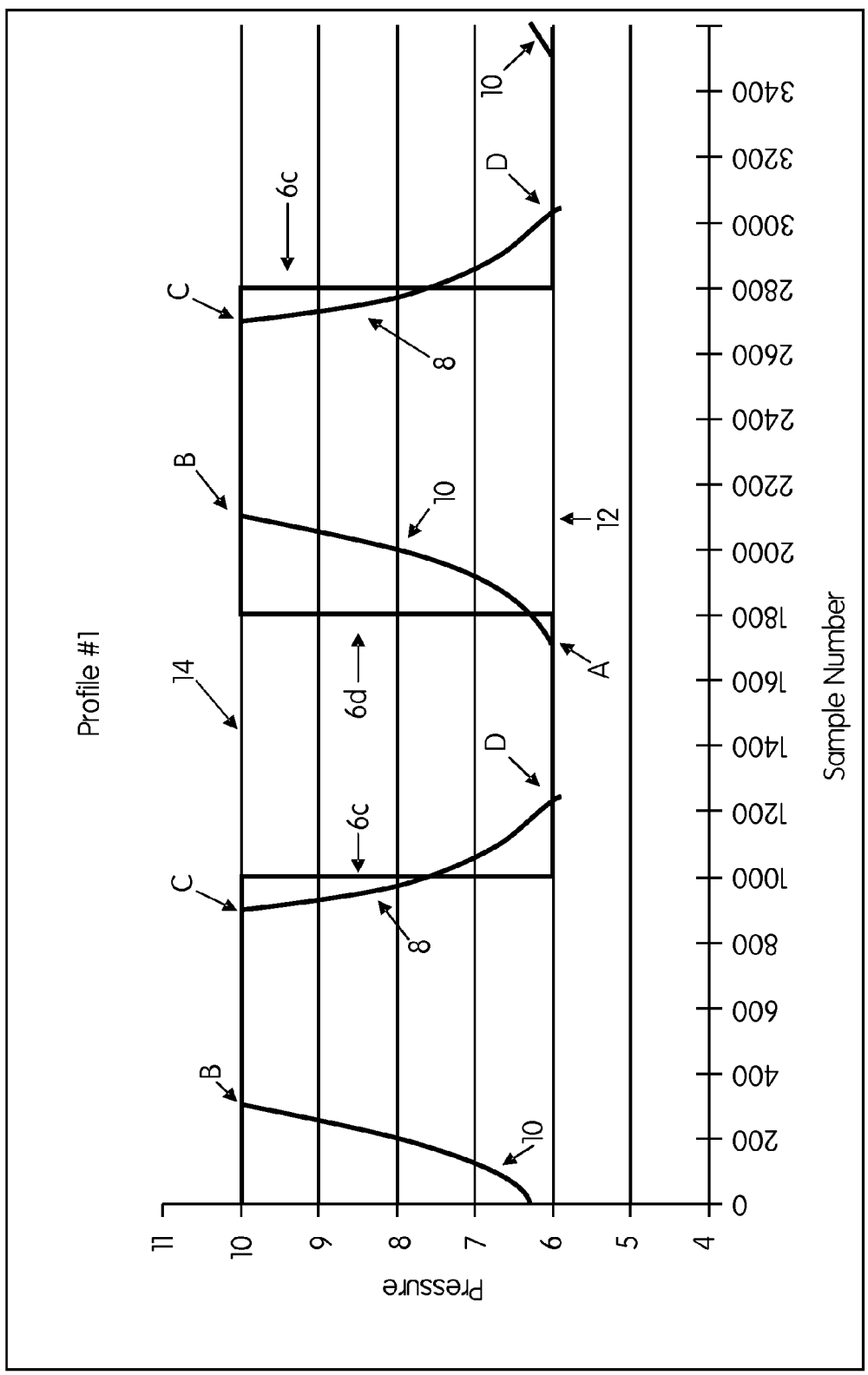
FIG. 5 shows a typical breathing cycle, showing inhale and exhale profiles #1 from FIGS. 2 and 3 respectively, showing the defined starting and ending points where the inhalation and exhalation profiles are applied to the overall breathing cycle.

FIGS. 3 and 4 show a graph of four possible inhalation and exhalation pressure profiles respectively expressed as a function of sample number, where the sample number represents the number of samples taken by pressure sensor 44 of the device, which enables the device to determine the actual times of the transitions between the phases of the breathing cycle, signaling the machine to adjust the pressure. Because the device takes samples at regular intervals, the sample number is equivalent to a measure of time passed for purposes of these figures.

FIG. 3 shows four possible inhalation profiles in accordance with the present invention. The inhalation profiles replace transition 6d between the EPAP pressure and IPAP pressure. In the preferred embodiment of the invention, the inhalation profiles are generated utilizing a third order polynomial of the form shown in Equation 1, although, in practice, the profiles may be customized by the use of any suitable polynomial to produce the desired profile.

$$Y = C_3 X^3 + C_2 X^2 + C_1 X + C_0 \tag{1}$$

FIG. 3 shows the inhalation profiles normalized to 1000 samples. The coefficients $C_0$-$C_3$ of the third order polynomial defining the profiles are preferably selected such that the profile starts at or near 0 (i.e., 0% between the EPAP and IPAP pressures) at sample 0 and ends at or near 1 (i.e., 100% of the way between the EPAP and IPAP pressures) at sample 1000. For samples between 0 and 1000, the result of calculating the polynomial results in a number representing a percentage between the EPAP and IPAP pressures (which may fall below the EPAP pressure or exceed the IPAP pressure). This allows the scaling of the transition profile based on the current EPAP and IPAP settings of the device.

The variable X in this equation represents the sample number within the transition pressure profile, and the equation and coefficients are set up to calculate the profile over a time period covering 1000 samples. Thus, if the transition pressure profile is to be applied over any period of time other than a period consisting of 1000 samples, the value of X will have to be scaled to the number of actual samples in the time period to account for the difference. The result of the equation, Y, is a number between 0 and 1 representing the percent between the EPAP and IPAP pressures for a given sample number X.

The coefficients for the inhalation profiles of the preferred embodiment are provided in Table 1 below. Although coefficients producing any inhalation profiles maybe utilized and still come within the scope of the invention, it is preferable that the inhalation profiles are selected which cause the equation to have a calculated value at or near 0 at sample 0 and a calculate value at or near 1 at sample 1000, that is, causing the transition pressure profile to start at the EPAP pressure (0%) and end up at the IPAP pressure (100%). The value of each point along the inhalation profile represents a percentage between the EPAP pressure and the IPAP pressure that is delivered to the patient during that particular time.

TABLE 1

| | Inhalation Phase Profile Coefficients | | | |
|---|---|---|---|---|
| | 1 | 2 | 3 | 4 |
| C3 | 1.00E−09 | 2.88E−09 | −6.00E−09 | 5.40E−09 |
| C2 | −3.00E−07 | −6.00E−06 | 0.000007 | −8.00E−06 |
| C1 | 0.0003 | 0.0041 | −0.0001 | 3.60E−03 |
| C0 | 0.0037 | 0.0187 | 0.0512 | 0.00E+00 |

The inhalation profiles are shown in FIG. 3 starting at a point labeled "A" and ending at a point labeled "B". The inhalation transition profiles will replace transition 6d between the EPAP pressure and the IPAP pressure, as shown in FIGS. 5-8. The actual positioning of points A and B on the pressure profile are adjustable and, as such, the inhalation profile must be scaled to the actual number of samples as specified by the placement of points A and B on the pressure profile. See, for example, the placement of points A and B in FIGS. 5-8, which show the four inhalation profiles integrated into the overall pressure profile.

Points A and B define the beginning and end respectively of the inhalation transition profile and are defined as follows.

Point A is a point during the exhalation phase (a percentage of the exhale phase) prior to the start of the expected transition to the inhale phase where the inhalation transition profile will be started.

Point B is a point during the inhalation phase (a percentage of the inhalation phase) after the transition from eth exhalation phase, where the inhalation transition profile will be ended.

For purposes of example, in FIGS. 5-8, point A has been selected as 10% and point B has been selected as 30%. Therefore, placement of the transition profile will begin 90% of the way into the exhalation phase and will last until 30% of the way into the inhalation phase. By way of example, if the exhalation phase is 800 sample in length, and the inhalation phase is 1000 samples in length, the inhalation transition pressure profile will start 80 samples (10% of 800) prior to the predicted end of the exhalation phase and will end 300 samples (30% of 1000) after the predicted start of the inhalation phase. Thus, the inhalation transition pressure profile will have an overall length of 380 samples. Because the coefficients are selected based on a normalized 1000 sample profile, in equation (1), the values of X will have to be scaled by multiplying the sample number (0 to 379) by (1000/380).

Note that, in general, once the actual lengths of the transition of the positioning of the transition pressure profiles are determined, and because the transition pressure profiles have been modeled to be 1000 samples in length, the sample number for use in equation (1) above can be scaled as follows:

$X$=sample number*(1000/length of transition pressure profile).

The selection of points A and B effect the duration of the transition profile, and, as such, the transition profile must be scaled over the expected number of samples between points A and B. The expected number of samples for each phase is estimated, as discussed below.

The exhalation transition pressure profiles of the preferred embodiment of the invention are shown in FIG. 4 and are generated by the same third order polynomial as utilized with the inhalation transition pressure profile, using different coefficients.

Because the exhalation transition pressure profiles replace transition 6c between the IPAP pressure and the EPAP pressure, it is preferable that the coefficients for the exhalation profile be selected such that at sample 0 (point C) the equation generates a value at or near 1 (i.e., 100% of the way between the EPAP and IPAP pressures, or, at the IPAP pressure) and at sample 1000 (point D) the equation generates a value at or near 0. (i.e., 0% between the EPAP and IPAP pressures, or, at the EPAP pressure), thus causing the transition pressure profile to start at the IPAP pressure and end up at the EPAP pressure.

As with the inhalation transition pressure profiles, the value of specific points along the exhalation profile represents a percentage for a given sample number between the EPAP and IPAP pressures. The coefficients generating the transition pressure profiles shown in FIG. 4 for the preferred embodiment of the invention are given in Table 2 below.

TABLE 2

| | Exhalation Phase Profile Coefficients | | | |
|---|---|---|---|---|
| | 1 | 2 | 3 | 4 |
| $C_3$ | −1.30E−09 | −4.80E−09 | −1.80E−09 | −4.10E−09 |
| $C_2$ | 3.00E−06 | 7.00E−06 | 1.00E−06 | 1.00E−05 |
| $C_1$ | −0.0027 | −3.20E−03 | −0.0002 | −0.0069 |
| $C_0$ | 0.9753 | 1.00E+00 | 1.0035 | 1.00E+00 |

Points C and D define the beginning and end respectively of the exhalation transition profile and are defined as follows.

Point C is a percentage from end of the inhalation cycle to the anticipated point of transition and Point D is a percentage in the exhalation cycle after the expected point of transition.

In FIGS. 5-8, point C has been selected as 10% and point D has been selected as 30%. Therefore, placement of the transition profile will begin 90% of the way into the inhalation phase and will last until 30% of the way into the exhalation phase. As before, if the inhalation phase is 1000 sample in length, and the exhalation phase is 800 samples in length, the exhalation transition pressure profile will start 100 samples (10% of 1000) prior to the predicted end of the inhalation phase and will end 240 samples (30% of 800) after the predicted start of the exhalation phase. Thus, the exhalation transition pressure profile will have an overall length of 340 samples. Because the coefficients are selected based on a normalized 1000 sample profile, in equation (1), the values of X will have to be scaled by multiplying the sample number (0 to 339) by (1000/340).

The application of the four inhalation and exhalation profiles shown in FIGS. 3 and 4 respectfully are shown in FIGS. 5-8. Note that it is not necessary that the inhalation and exhalation transition pressure profiles "match" with each other. Of the four inhalation transition pressure profiles and exhalation transition pressure profiles shown as the preferred embodiment of the invention, any combination of inhalation and exhalation transition pressure profiles may be selected.

Figure 6:
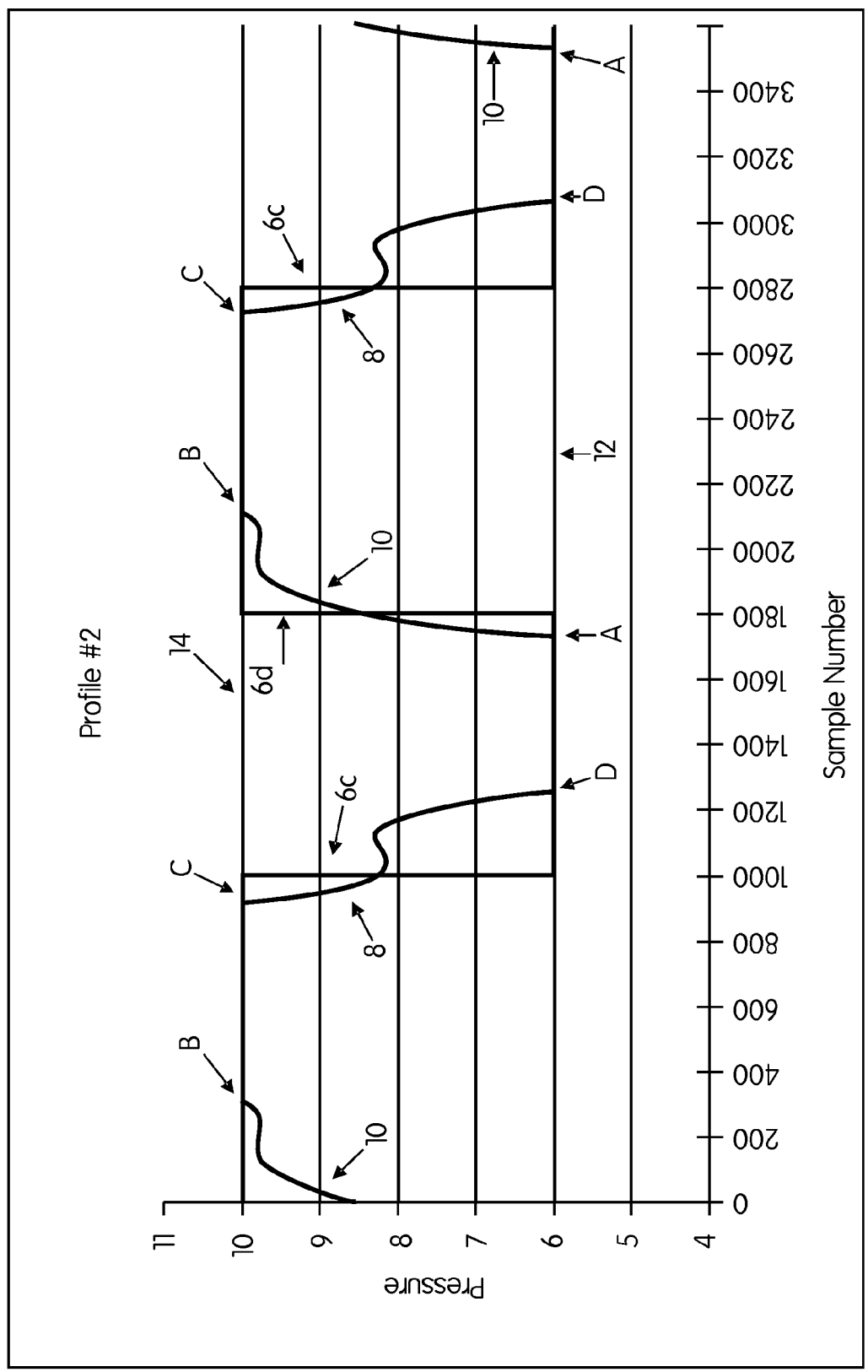
FIG. 6 is similar to FIG. 4, but shows inhale and exhale profiles #2 from FIGS. 3 and 4 respectively.
Figure 7:
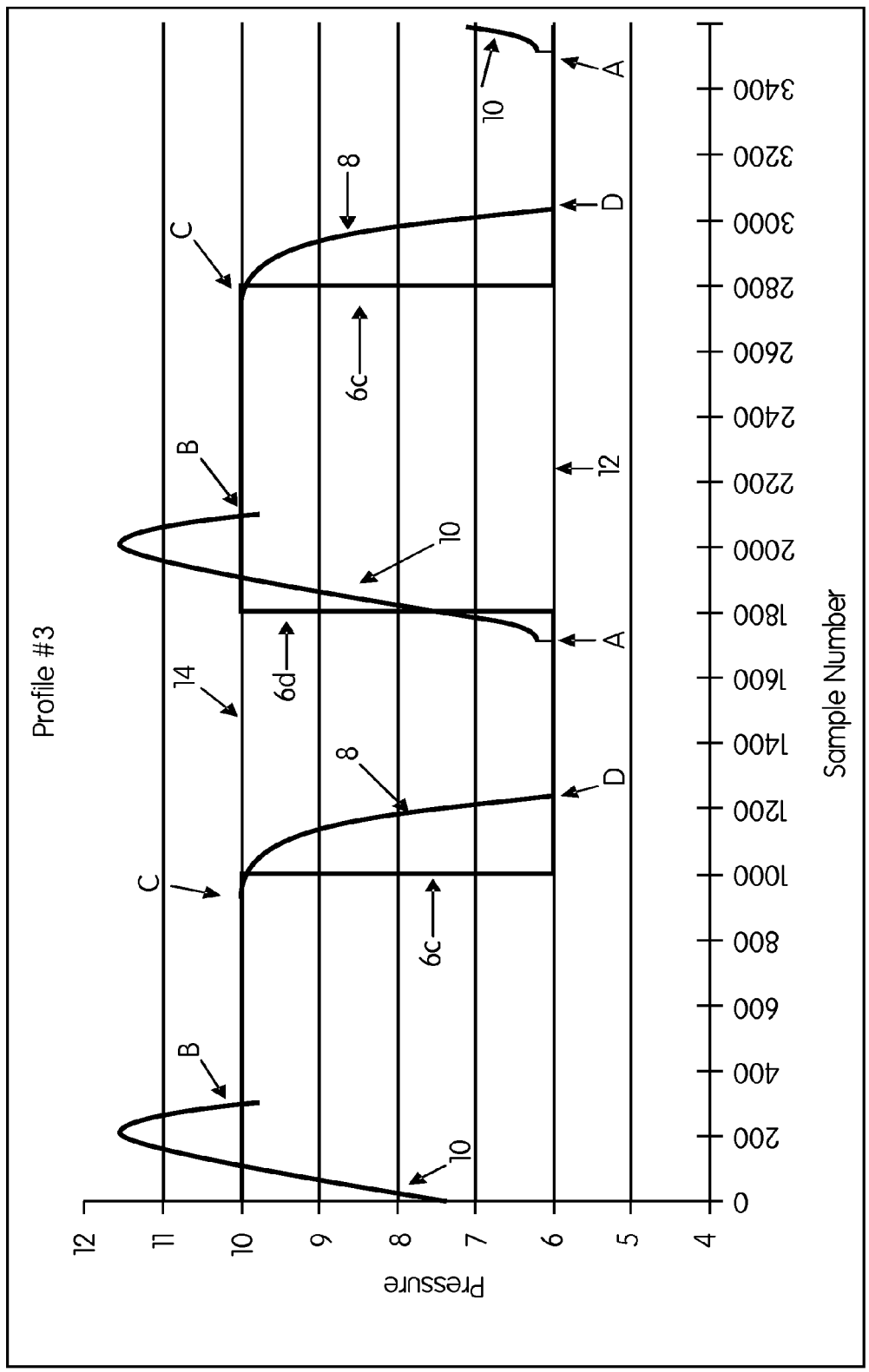
FIG. 7 is similar to FIG. 4, but shows inhale and exhale profiles #3 from FIGS. 3 and 4 respectively.
Figure 8:
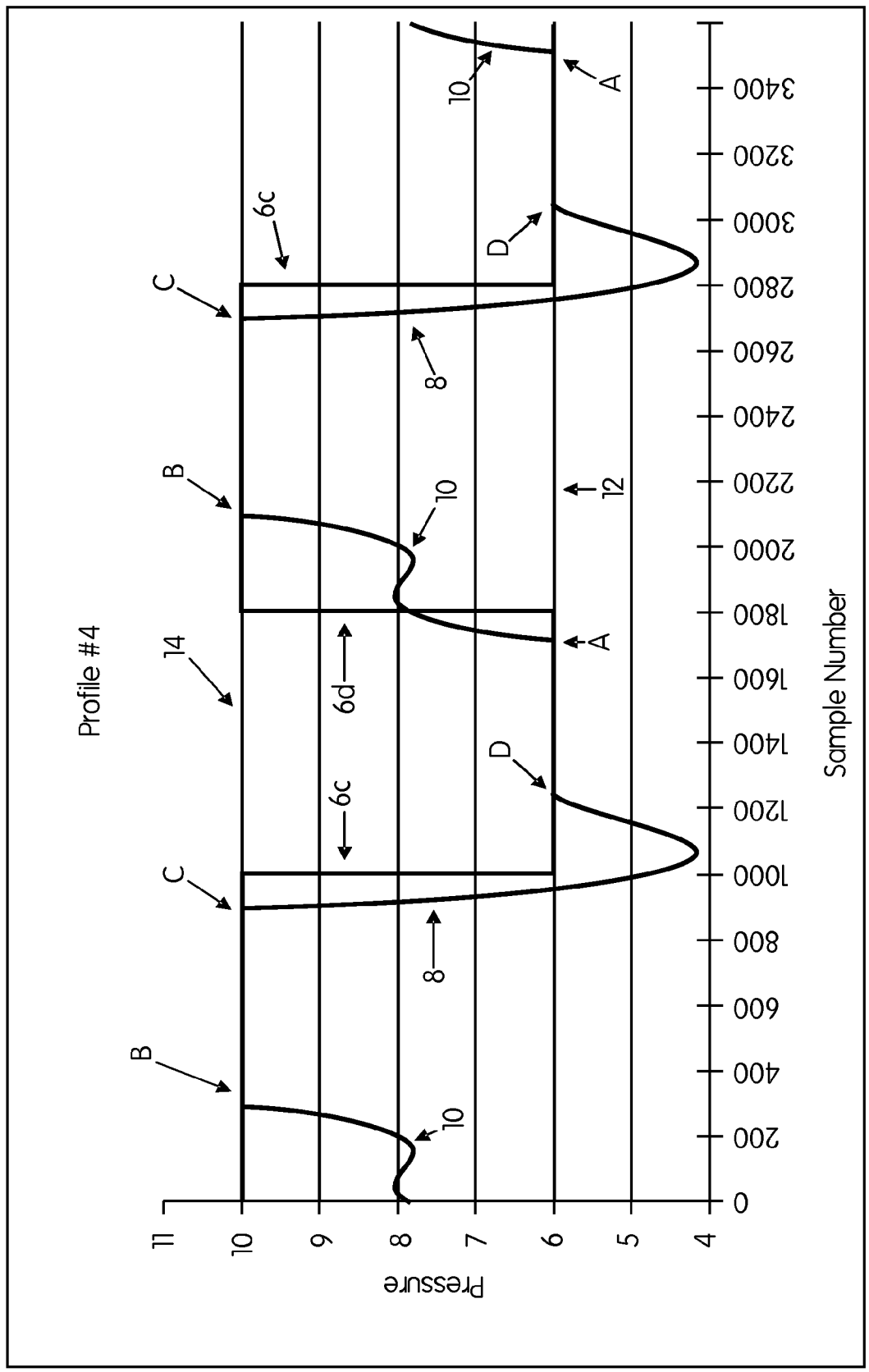
FIG. 8 is similar to FIG. 4, but shows inhale and exhale profiles #4 from FIGS. 3 and 4 respectively.

For purposes of explanation refer to FIG. 6, which shows the inhalation transition pressure profile #2 and exhalation transition pressure profile #2 as applied to a standard overall bi-level pressure profile.

In FIG. 6, the inhalation transition pressure profile is shown extending between points A and B and is identified by reference number 10 while the exhalation transition pressure profile is shown extending between points C and D and is identified by reference number 8. The length of the breathing cycle is shown as being 1800 samples (exhalation phase of 800 samples and inhalation phase of 1000 samples), however, the actual length of the breathing cycle will vary with each individual user of the device. The device will estimate the length of each breathing cycle, and the specific lengths of the inhalation phase and exhalation phase, which, as shown, are not necessarily equal in length, based on the length of one or more previous breathing cycles. In one embodiment of the invention the length of the previous breathing cycle is utilized or, alternatively, a moving average of the last several breathing cycles may be utilize to predict the length of the next breathing cycle.

Preferably, points A, B, C, and D, will be settable by a user or the user's therapist as a percentage of the length of the actual phases of the breathing cycle. The basis for calculating the actual placement of A, B, C and D, however, for the start and ending point of the inhalation and exhalation transition pressure profiles is the estimation of the length of the cycle based upon previous cycles. In the examples in FIGS. 5-8 the inhalation phase of the cycle is shown as being 1000 samples in length while the exhalation phase of the cycle is only 800 samples in length.

It should also be noted as well that the IPAP pressure 14 and EPAP pressure 12 are settable by either the user or a therapist for each individual user and for purposes of these examples, have been set to 10 cmH$_2$O and 6 cmH$_2$O respectively. As such, the inhalation and exhalation profiles must be scaled not only to take into account differing lengths of the breathing cycle and different positions of points A, B, C and D but also to account for differing IPAP and EPAP pressures.

For the period of time not covered by the transition pressure profiles, the standard IPAP pressure 14 and EPAP pressure 12 are applied. Note, however that points A, B, C and D maybe adjusted such that points B and C coincide and points D and A coincide and therefore it may be the case that the overall pressure profile is always in transition between the IPAP and EPAP pressures.

As previously noted, the transitions between the phases of the breathing cycles are estimated based upon previous breathing cycles. It is possible that the actual detected transition between the phases (i.e., the device detects that the user has started the next phase) may occur prior to the time when the transition pressure profile is started. For example, transition 6c from the IPAP pressure to the EPAP pressure may actually occur before point C. In such an occurrence, the transition pressure profile will start from the point where it intersects the transition 6c. For example, the inhalation phase in our examples is estimated to be 1,000 samples in length and the transition profile was to begin at the 900th sample. At any time during the inhale phase prior to the 900th sample, if the actual exhale transition is detected, the algorithm will set the sample count to 1000 and will continue the application of the exhalation transition pressure profile from that point until the EPAP pressure is reached, even if point D occurs prior to its scheduled sample number. This accelerates the decline of the pressure from the IPAP pressure to the EPAP pressure. The same thing occurs on the transition between the EPAP pressure and the IPAP pressure, when the inhalation transition pressure profile is being applied.

It should be noted that any or all of the variables discussed may be settable in some embodiments by a user of the device, or may be fixed by the manufacturer of the device. For example, points A, B, C, and D may be factory set, or the user may have the ability to set them. Likewise, the coefficients of the transition pressure profiles may be limited to the four preferred profiles, may be limited to other sets of coefficients, or may be settable by a user (or the user's therapist) of the device. As for the third order polynomial used to calculate the transition pressure profile curves, in alternate embodiments, other equations may be substitute and will still be within the scope of the invention. The third order polynomial given is only an exemplar for the preferred embodiment of the invention. In preferred embodiments of the invention, the device is designed such that the algorithms controlling the overall pressure profile may be field updateable via a software update.

I claim:

1. A method of setting the pressure at which breathing gas is delivered by a breathing therapy device comprising the steps of:
   a. receiving or calculating a first therapy pressure and a second therapy pressure;
   b. predicting a time for transition between said first therapy pressure and said second therapy pressure;
   c. calculating a transition pressure profile to be applied for transitions between said first therapy pressure and said second therapy pressure;
   d. scaling said transition pressure profile to a desired duration, said desired duration starting at a set time prior to said predicted transition time and ending at a set time after said predicted transition time; and
   e. modifying said pressure at which said breathing gas is delivered in accordance with said scaled transition pressure profile to transition said pressure from said first therapy pressure to said second therapy pressure.

2. The method of claim 1 wherein said calculated transition pressure profile for transitions for transitions from said first therapy pressure to said second therapy pressure is independent of said calculated transition pressure profile for transitions from said second therapy pressure to said first therapy pressure.

3. The method of claim 1 further comprising the steps of:
   a. collecting and storing one or more actual transition times; and
   b. predicting said time of transition based on one or more of said actual transition times.

4. The method of claim 1 further comprising the steps of:
   a. detecting an actual time of transition between said first therapy pressure and said second therapy pressure; and
   b. if said actual transition time precedes said predicted transition time, altering the pressure delivered in accordance with the point on the transition pressure profile that was to be delivered at said predicted transition time, and thereafter, delivering pressure in accordance with said transition pressure profile.

5. The method of claim 1 wherein said set time prior to said predicted transition and set time after said predicted transition are independently adjustable.

6. The method of claim 1 wherein said transition pressure profile has a shape and is calculated using a polynomial and further wherein said shape of said transition pressure profile is determined by a set of coefficients used in the calculation of said polynomial.

7. The method of claim 6 wherein said polynomial is of the form:

$$Y=C_3X^3+C_2X^2+C_1X+C_0$$

wherein X is a time-related variable;
wherein $C_0$, $C_1$, $C_2$ and $C_3$ are said coefficients defining said shape of said transition pressure profile, and
wherein Y is a percentage between said first therapy pressure and said therapy second pressure.

8. The method of claim 6 wherein a plurality of said sets of coefficients are stored in of said device and further wherein one set of coefficients is selected for a transition from said first therapy pressure to said second therapy pressure and a different set of coefficients is selected for a transition from said second therapy pressure to said first therapy pressure.

9. The method of claim 6 wherein said set of coefficients may be selected or entered by a user of the device.

10. The method of claim 1 wherein said set times prior to and after said predicted transition time are adjustable and independent.

11. The method of claim 5 wherein said transition pressure profile is scaled for said duration between said set time prior to said predicted transition time and said set time after said predicted transition time.

12. The method of claim 1 wherein said method further comprises the step of modifying the pressure at which breathing gas is delivered to a user of said device during transitions between said first pressure and said second pressure in accordance with the calculated transition pressure profile.

13. The method of claim 1 wherein a first transition pressure profile is calculated for transitions from said first therapy pressure to said second therapy pressure, and a second transition pressure profile is calculated for transitions from said second therapy pressure to said first therapy pressure.

* * * * *